United States Patent [19]

Dusza et al.

[11] 4,451,479

[45] May 29, 1984

[54] THERAPEUTICALLY ACTIVE 3-AMINO-1-HALOGENATED PHENYL-2-PYRAZOLINES AND THEIR C4 AND C5 ANALOGS

[75] Inventors: John P. Dusza, Nanuet, N.Y.; Joseph P. Joseph, Montvale, N.J.; Seymour Bernstein, New City, N.Y.

[73] Assignee: American Cyanamid Company, Stamford, Conn.

[21] Appl. No.: 432,607

[22] Filed: Oct. 4, 1982

Related U.S. Application Data

[63] Continuation-in-part of Ser. No. 282,700, Jul. 13, 1981, abandoned.

[51] Int. Cl.$^3$ .................... A61K 31/415; A01N 43/56; C07D 231/06

[52] U.S. Cl. .................................. 424/273 P; 548/362

[58] Field of Search ...................... 424/273 P; 548/362

[56] References Cited

FOREIGN PATENT DOCUMENTS 22578 1/1981 European Pat. Off. ............ 548/362

OTHER PUBLICATIONS

Radmark et al., FEBS Letters 1980, vol. 110, pp. 213–215.

Nijkamp et al., Eur. J. Pharmacol. 1980, vol. 62, pp. 121–122.

*Primary Examiner*—Richard Raymond

*Attorney, Agent, or Firm*—Anne M. Rosenblum

[57] ABSTRACT

A method of meliorating the inflammation and/or the progressive joint deterioration characteristic of arthritic disease, preventing the onset of asthmatic symptoms and allergic diseases, treating pain or treating bacterial and fungal infections in mammals using 3-amino-1-halogenated phenyl-2-pyrazolines and their C4 and C5 analogs.

58 Claims, No Drawings

THERAPEUTICALLY ACTIVE 3-AMINO-1-HALOGENATED PHENYL-2-PYRAZOLINES AND THEIR C4 AND C5 ANALOGS

CROSS REFERENCE TO RELATED APPLICATION

This application is a continuation-in-part of our co-pending application, Ser. No. 282,700, filed July 13, 1981, now abandoned.

PRIOR ART

1. R. Battisti, et. al., U.S. Pat. No. 4,149,005 (Apr. 10, 1979) discloses compounds of the formula:

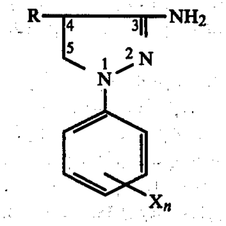

where R is H or $CH_3$, X is H, Br, Cl, alkyl, alkoxy or carboxyalkyl groups with from 1 to 4 carbon atoms or $CF_3$; and n is 1 or 2. These are disclosed as being used as intermediates in the preparation of 1-phenyl-3-aminopyrazoles as coupling components in azo dye manufacture. Related foreign patents: Ger. Offen. No. 2,727,706; French No. 2,355,834; Gr. Br. No. 1,515,500; Belgium No. 855,944; Netherland No. 7,706,760 and Japan No. 28,168.

2. G. A. Higgs, et. al., (Wellcome Research Laboratories) Biochemical Pharmacology, 28 1959 (1979) discloses 3-amino-1-[m-(trifluoromethyl)phenyl]-2-pyrazoline (BW 755C);

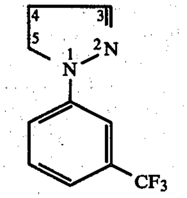

(BW 755C)

This compound is reported to have anti-inflammatory activity.

DESCRIPTION OF THE INVENTION

This invention is concerned with certain pyrazoline compounds useful for treating pain and meliorating inflammation as well as for the control of bacterial and/or fungal infections in mammals. They are also useful for inhibiting the progression of arthritis and joint deterioration or preventing the onset of allergic diseases. These compounds are certain 3-amino-1-halogenated phenyl-2-pyrazoline compounds of the formula

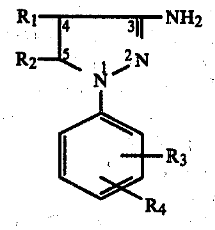

I wherein $R_1$ is hydrogen or lower alkyl ($C_1$–$C_4$); $R_2$ is hydrogen, lower alkyl ($C_1$–$C_4$), phenyl or

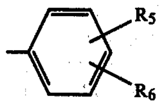

where $R_5$ and $R_6$ are the same or different and are hydrogen, halogen or lower alkyl ($C_1$–$C_4$) with the proviso that $R_5$ and $R_6$ cannot both be hydrogen; $R_3$ and $R_4$ are the same or different and are hydrogen or halogen with the proviso that $R_3$ and $R_4$ cannot both be hydrogen; and the pharmacologically acceptable acid-addition salts thereof.

Preparation of the compounds of this invention, which are useful in the above-mentioned methods of treatment, is accomplished by an adaptation of the procedure of Duffin, G. F. and Kendall, J. D., J. Chem. Soc., 1954, 408; in accordance with the following scheme:

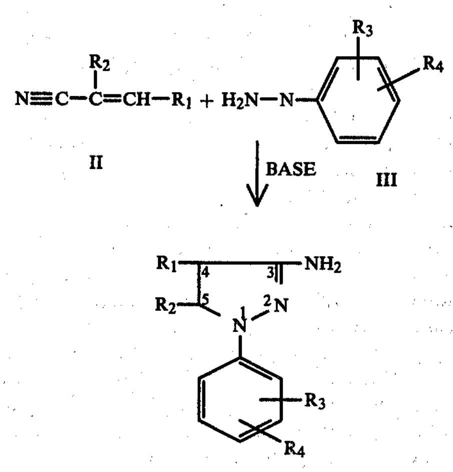

II

III

I wherein $R_1$ and $R_2$ are as defined for Formula I above.

In accordance with above a 2-hydrazino compound of Formula III is reacted with the appropriate $\alpha,\beta$-unsaturated Module II in a base catalyzed condensation procedure which is catalyzed with a base such as sodium ethoxide or choline hydrate in a suitable solvent, such as absolute ethanol. The reaction mixture is preferably refluxed for 4–16 hours, then, preferably the solvent is reduced in volume, and the precipitate is collected by filtration and purified in accordance with standard procedures.

The compounds of the instant invention have utility as pharmacological agents. They are active either as anti-inflammatory agents, analgesic agent, antibacterial and/or antifungal agents and in some cases are active in more than one of these areas. Some of the compounds of this invention are further useful in inhibiting the progression of arthritis such as rheumatoid arthritis and inhibiting the progression of joint deterioration or preventing the onset of asthma and other allergic diseases. They also find utility in the amelioration or prevention of pathological reactions such as osteoarthritis, gout, acute synovitis and psoriasis.

Representative compounds of the present invention have proven to be active in vivo as anti-inflammatory agents when tested by the Carageenin Induced Edema of the Rat Paw Test. This test is a modification of the method of Winter, C. A., et al., Proc. Soc. Exp. Biol. and Med., 111, 544 (1962). Compounds found to be active in this test are:

3-Amino-1-(3,4-dichlorophenyl)-2-pyrazoline
3-Amino-1-(m-fluorophenyl)-4-methyl-2-pyrazoline
3-Amino-1-(m-fluorophenyl)-2-pyrazoline
3-Amino-1-(3,4-dichlorophenyl)-4-methyl-2-pyrazoline
3-Amino-1,5-bis(p-chlorophenyl)-2-pyrazoline
3-Amino-1-(2,4-dichlorophenyl)-2-pyrazoline
3-Amino-1-(m-chlorophenyl)-2-pyrazoline
3-Amino-1-(3,4-dichlorophenyl)-5-methyl-2-pyrazoline
3-Amino-1-(p-fluorophenyl)-2-pyrazoline
3-Amino-1-(p-fluorophenyl)-5-methyl-2-pyrazoline
3-Amino-1-(m-fluorophenyl)-5-methyl-2-pyrazoline
3-Amino-1-(3,4-dichlorophenyl)-5-methyl-2-pyrazoline sulfate (2:1)
3-Amino-1-(p-fluorophenyl)-5-methyl-2-pyrazoline sulfate (2:1)
3-Amino-1-(p-chlorophenyl)-5-methyl-2-pyrazoline
3-Amino-1-(p-chlorophenyl)-5-ethyl-2-pyrazoline
3-Amino-1-(3,4-dichlorophenyl)-5-ethyl-2-pyrazoline
3-Amino-5-ethyl-1-(p-fluorophenyl)-2-pyrazoline
3-Amino-1-(p-chlorophenyl)-4-methyl-2-pyrazoline
3-Amino-1-(m-chlorophenyl)-4-methyl-2-pyrazoline
3-Amino-5-butyl-1-(p-fluorophenyl)-2-pyrazoline
3-Amino-5-butyl-1-(p-chlorophenyl-2-pyrazoline
3-Amino-4-butyl-1-(p-chlorophenyl)-2-pyrazoline
3-Amino-1-(p-chlorophenyl)-5-propyl-2-pyrazoline
3-Amino-1-(3-chloro-p-tolyl)-5-methyl-2-pyrazoline
3-Amino-1-(m-fluorophenyl)-5-ethyl-2-pyrazoline
3-Amino-1-(p-fluorophenyl)-5-phenyl-2-pyrazoline
3-Amino-1-(p-chlorophenyl)-5-phenyl-2-pyrazoline Another in vivo method of determining drug effect on conditions which result in the production of pain is measuring the effect on ultraviolet induced erythema in guinea pigs [Winder, C. V., et. al., A Study of Pharmacological Influences on Ultraviolet Erythema in Guinea Pigs, Arch. Int. Pharmacodyn., 116 261(1958)]. Representative compounds of the present invention which are active when tested by the ultraviolet induced erythema test are:

3-Amino-1-(3,4-dichlorophenyl)-2-pyrazoline
3-Amino-1-(m-fluorophenyl)-4 methyl-2-pyrazoline
3-Amino-1-(m-fluorophenyl)-2-pyrazoline
3-Amino-1-(2,4-dichlorophenyl)-2-pyrazoline
3-Amino-1-(m-chlorophenyl)-2-pyrazoline
3-Amino-1-(3,4-dichlorophenyl)-5-methyl-2-pyrazoline
3-Amino-1-(p-fluorophenyl)-2-pyrazoline
3-Amino-1-(p-chlorophenyl)-5-methyl-2-pyrazoline
3-Amino-1-(p-chlorophenyl)-5-ethyl-2-pyrazoline
3-Amino-5-ethyl-1-(p-fluorophenyl)-2-pyrazoline
3-Amino-1-(p-chlorophenyl)-4-methyl-2-pyrazoline
3-Amino-1-(m-chlorophenyl)-4-methyl-2-pyrazoline
3-Amino-5-butyl-1-(p-fluorophenyl)-2-pyrazoline
3-Amino-5-butyl-1-(p-chlorophenyl)-2-pyrazoline
3-Amino-4-butyl-1-(p-chlorophenyl)-2-pyrazoline
3-Amino-1-(m-fluorophenyl)-5-ethyl-2-pyrazoline A test used to show activity against chronic inflammation in adjuvant arthritis is a modification of the technique of Newbold, B., "Chemotherapy of Arthritis Induced In Rats by Mycobacterial Adjuvant", Brit. J. Pharmacol. Chemother., 21, 127 (1963), which is described in U.S. Pat. No. 3,863,010. Representative compounds of the present invention accepted as active when tested by the Adjuvant Arthritis Test are:

3-Amino-1-(3,4-dichlorophenyl)-2-pyrazoline
3-Amino-1-(m-fluorophenyl)-4-methyl-2-pyrazoline
3-Amino-1-(m-fluorophenyl)-2-pyrazoline
3-Amino-1-(p-chlorophenyl)-2-pyrazoline
3-Amino-1-(2,4-dichlorophenyl)-2-pyrazoline
3-Amino-1-(m-chlorophenyl)-2-pyrazoline
3-Amino-1-(3,4-dichlorophenyl)-5-methyl-2-pyrazoline
3-Amino-1-(p-fluorophenyl)-2-pyrazoline
3-Amino-1-(p-fluorophenyl)-4-methyl-2-pyrazoline
3-Amino-1-(p-fluorophenyl)-5-methyl-2-pyrazoline
3-Amino-1-(p-chlorophenyl)-5-methyl-2-pyrazoline
3-Amino-5-(p-chlorophenyl)-1-(p-fluorophenyl)-2-pyrazoline
3-Amino-1-(p-chlorophenyl)-5-ethyl-2-pyrazoline
3-Amino-5-ethyl-1-(p-fluorophenyl)-2-pyrazoline
3-Amino-1-(m-fluorophenyl)-5-ethyl-2-pyrazoline
3-Amino-1-(p-fluorophenyl)-5-phenyl-2-pyrazoline The compounds of the present invention also possess activity as analgesic agents. A method employed for measuring the in vivo activity of the compounds of the present invention is the "writhing syndrome" test for analgesic activity as described by Siegmund, et al., Proceedings of the Society for Experimental Biology and Medicine, 95, 729 (1957), with modifications as described in U.S. Pat. No. 3,863,010. Representative compounds of the present invention which are active when tested by the "writhing syndrome" test are listed as follows:

3-Amino-1-(3,4-dichlorophenyl)-2-pyrazoline
3-Amino-1-(2,5-dichlorophenyl)-2-pyrazoline
3-Amino-1-(p-chlorophenyl)-2-pyrazoline
3-Amino-1-(3,4-dichlorophenyl)-2-pyrazoline, hydrochloride
3-Amino-5-(p-chlorophenyl)-1-(m-fluorophenyl)-2-pyrazoline
3-Amino-1-(3,4-dichlorophenyl)-5-p-tolyl-2-pyrazoline
3-Amino-1,5-bis(3,4-dichlorophenyl)-2-pyrazoline
3-Amino-1-(p-chlorophenyl)-5-propyl-2-pyrazoline
3-Amino-1-(3-chloro-p-tolyl)-5-methyl-2-pyrazoline
3-Amino-1-(m-fluorophenyl)-5-ethyl-2-pyrazoline
3-Amino-1-(p-fluorophenyl)-5-phenyl-2-pyrazoline
3-Amino-1-(p-chlorophenyl)-5-phenyl-2-pyrazoline Another method measuring the in vivo analgesic activity of the compounds of the present invention is the Rat Paw Pain Test. This test is a modification of the method of Randall and Selitto [Arch. Int. Pharmacodyn., 111, 409 (1957)] as described in U.S. Pat. No. 3,863,010. The following compounds were tested and found to be active by this test:

3-Amino-1-(m-fluorophenyl)-2-pyrazoline
3-Amino-5-ethyl-1-(p-fluorophenyl)-2-pyrazoline Representative compounds of the present invention have been proven active in vitro as antibacterial and/or antifungal agents when tested by such procedures as the standard agar dilution procedure. Compounds proven active in this test include:

3-Amino-1-(m-chlorophenyl)-5-phenyl-2-pyrazoline
3-Amino-1-(3,4-dichlorophenyl)-2-pyrazoline
3-Amino-1-(m-fluorophenyl)-4-methyl-2-pyrazoline
3-Amino-1-(m-fluorophenyl)-2-pyrazoline 3-Amino-1-(m-fluorophenyl)-5-phenyl-2-pyrazoline
3-Amino-1-(3,4-dichlorophenyl)-4-methyl-2-pyrazoline
3-Amino-1-(3,4-dichlorophenyl)-5-phenyl-2-pyrazoline
3-Amino-1-(3,5-dichlorophenyl)-2-pyrazoline
3-Amino-1,5-bis(p-chlorophenyl)-2-pyrazoline
3-Amino-1-(2,5-dichlorophenyl)-2-pyrazoline
3-Amino-1-(p-chlorophenyl)-2-pyrazoline
3-Amino-1-(3,4-dichlorophenyl)-2-pyrazoline, hydrochloride
3-Amino-1-(2,4-dichlorophenyl)-2-pyrazoline
3-Amino-1-(m-chlorophenyl)-2-pyrazoline
3-Amino-1-(3,4-dichlorophenyl)-5-methyl-2-pyrazoline
3-Amino-1-(p-fluorophenyl)-2-pyrazoline
3-Amino-1-(p-fluorophenyl)-4-methyl-2-pyrazoline
3-Amino-5-(p-chlorophenyl)-1-(3,4-dichlorophenyl)-2-pyrazoline
3-Amino-5-(p-chlorophenyl)-1-(m-fluorophenyl)-2-pyrazoline
3-Amino-1-(3,4-dichlorophenyl)-5-p-tolyl-2-pyrazoline
3-Amino-1-(p-fluorophenyl)-5-methyl-2-pyrazoline
3-Amino-1-(m-fluorophenyl)-5-methyl-2-pyrazoline
3-Amino-1-(3,4-dichlorophenyl)-5-methyl-2-pyrazoline, sulfate (2:1)
3-Amino-1-(p-fluorophenyl)-5-methyl-2-pyrazoline, sulfate (2:1)
3-Amino-1-(p-chlorophenyl)-5-methyl-2-pyrazoline
3-Amino-1,5-bis(3,4-dichlorophenyl)-2-pyrazoline
3-Amino-5-(p-chlorophenyl)-1-(p-fluorophenyl)-2-pyrazoline
3-Amino-1-(p-chlorophenyl)-5-ethyl-2-pyrazoline
3-Amino-1-(3,4-dichlorophenyl)-5-ethyl-2-pyrazoline
3-Amino-5-ethyl-1-(p-fluorophenyl)-2-pyrazoline
3-Amino-1-(p-chlorophenyl)-4-methyl-2-pyrazoline
3-Amino-1-(m-chlorophenyl)-4-methyl-2-pyrazoline
3-Amino-5-butyl-1-(p-chlorophenyl)-2-pyrazoline
3-Amino-1-(3-chloro-p-tolyl)-5-methyl-2-pyrazoline
3-Amino-1-(m-fluorophenyl)-5-ethyl-2-pyrazoline
3-Amino-1-(p-fluorophenyl)-5-phenyl-2-pyrazoline
3-Amino-1-(p-chlorophenyl)-5-phenyl-2-pyrazoline The compounds of the present invention have been found to be highly useful for the above pharmaceutical therapy, when administered in amounts ranging from about 0.5 milligram to about 250 mg. per kilogram of body weight per day. A preferred dosage regimen for optimum results would be from about 5 mg to about 100 mg per kilogram of body weight per day, and such dosage units are employed that a total of from about 0.35 g to about 7.0 g of the active ingredient for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, intraarticular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chloro-phenyl-$\alpha$-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, exlixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives a dye and flavoring such as cherry or orange flavor. Of course, any material used in preparing any dosage unit form should be pharmaceutically pure and substantially non-toxic in the amounts employed.

For the control of asthma or allergic responses, the active ingredient may also be administered by inhalation. For the inhalation routes, an inhaler device may be employed with the active ingredient in a suitable form such as powder or solution with appropriate pharmaceutical carriers.

This invention will be described in greater detail in conjunction with the following examples.

EXAMPLE 1

3-Amino-1-(m-chlorophenyl)-5-phenyl-2-pyrazoline

A 0.6 g. amount of sodium metal is dissolved in 100 ml. of absolute ethanol, then 14.76 g. of m-chlorophenylhydrazine is added followed in 5 minutes by 12.92 g. of cinnamonitrile. The reaction mixture is refluxed for 6 hours, then cooled in an ice-bath. The precipitate formed is collected by filtration, then is dissolved in dichloromethane. This solution is passed through a short column of a hydrous magnesium silicate. The effluent is heated to reflux on a steam bath and hexane is added until a precipitate occurs. The product is collected, then is recrystallized from dichloromethane-hexane to give 7.55 g. of the product of the Example as salmon colored needles, m.p. 164°-165° C.

EXAMPLE 2

3-Amino-1-(3,4-dichlorophenyl)-2-pyrazoline

A 2.8 g. amount of sodium metal is dissolved in 200 ml. of absolute ethanol, then 21.35 g. of 3,4-dichlorophenylhydrazine hydrochloride is added followed in 10 minutes by 5.5 g. of acrylonitrile. The reaction mixture is refluxed for 4 hours then most of the ethanol is removed in vacuo. Water is added to separate a solid. The solid is collected by filtration and dried. The solid is dissolved in methanol, treated with activated charcoal and filtered. The filtrate is evaporated to give a solid. The solid is recrystallized from methanol to give the desired product as tan crystals, m.p. 182°-183.5° C.

EXAMPLE 3

3-Amino-1-(m-fluorophenyl)-4-methyl-2-pyrazoline

A 1.38 g. amount of sodium metal is dissolved in 150 ml. of absolute ethanol, then 8.1 g. of m-fluorophenylhydrazine hydrochloride is added followed by 3.9 g. of methacrylonitrile. The reaction mixture is refluxed for 5 hours, then is evaporated to dryness in vacuo. Water is added to give a dark semi-solid precipitate. The aqueous is decanted then more water is added and the solid is collected by filtration. The solid is dissolved in dichloromethane and the solution is passed through a short column of a hydrous magnesium silicate. The effluent is evaporated to give an oil. The oil is dissolved in hexane, treated with activated charcoal and filtered and evaporated to give a solid. The solid is recrystallized from hexane to give 0.65 g. of the desired product as light orange prisms, m.p. 78°-80° C.

EXAMPLE 4

3-Amino-1-(m-fluorophenyl)-2-pyrazoline

A 1.38 g. amount of sodium metal is dissolved in 150 ml. of absolute ethanol, then 8.1 g. of m-fluorophenylhydrazine hydrochloride is added followed in 15 minutes by 2.75 g. of acrylonitrile. The reaction mixture is refluxed for 5 hours, then is evaporated to dryness in vacuo. Water is added and the separated solid is collected by filtration. The solid is dissolved in dichloromethane and the solution is passed through a short column of a hydrous magnesium silicate. The effluent is heated to reflux on a steam bath and hexane is added to precipitate a product. The solid is collected, dissolved in acetone, treated with activated charcoal and filtered. Hexane is added to the filtrate to crystallize 2.95 g. of the product of the Example as off-white needles, m.p. 146°-147° C.

EXAMPLE 5

3-Amino-1-(m-fluorophenyl)-5-phenyl-2-pyrazoline

The procedure of Example 4 is followed substituting 6.46 g. of cinnamonitrile for 2.75 g. of acrylonitrile to give 4.75 g. of the desired product as pale yellow prisms, m.p. 165°-166° C.

EXAMPLE 6

3-Amino-1-(3,4-dichlorophenyl)-2-pyrazoline hydrochloride

A 1.65 g. amount of 3-amino-1-(3,4-dichlorophenyl)-2-pyrazoline (prepared as described in Example 2) is dissolved in 5.0 ml. of concentrated hydrochloric acid then methanol is added and the solvents are evaporated in vacuo. The residue is triturated with ether several times then acetone is added to crystallize the product. The product of the Example is collected by filtration and washed with ether to give 1.65 g. as colorless crystals, m.p. 170°-175° C. (dec.).

EXAMPLE 7

3-Methoxyvaleronitrile

A 248 g. amount of sodium methylate is dissolved in a solution of 828 g. of methanol diluted with 102 ml. of N,N-dimethylformamide. The above solution is added via a dropping funnel to a stirred solution of 200 g. of diethylcyanomethylphosphonate and 70.0 g. of propionaldehyde in 150 ml. of N,N-dimethylformamide, cooled in an ice-bath at 40°-45° C. After the addition is complete the mixture is warmed to 50° C. and stirring is continued for one hour without further warming or cooling.

The reaction mixture is diluted with 540 ml. of a 50:50 mixture of methanol:water, then the pH of the solution is adjusted to pH 7.0 with glacial acetic acid. The neutral solution is copiously extracted with ether and the combined ether extracts are back washed with water. The organic solution is dried over anhydrous magnesium sulfate, filtered and concentrated under reduced pressure to give an oil. The oil is distilled through a 24 inch saddle filled column, b.p. 50° C./9-10 mm. (oil bath temperature 135°-145° C.), to yield a colorless liquid. The crude product is dissolved in ether and washed 3 times with water. The organic solvent is evaporated in vacuo to yield 26.0 g. of the desired product as a colorless liquid.

EXAMPLE 8

2-Heptenenitrile

To 500 ml. of warm freshly distilled benzene is added 14.3 g. of valeraldehyde and 50.0 g. of (triphenylphosphoranylidene)acetonitrile. The stirred mixture is heated at reflux under nitrogen for 6 hours, then is allowed to stand at room temperature for 48 hours. The reaction solution is washed twice with 100 ml. portions of 5% sodium bisulfite and 5% sodium bicarbonate then is washed with water. The solution is dried over anhydrous magnesium sulfate then is evaporated to dryness leaving a solid and a thin oil. The solid is extracted several times with hexane. The combined hexane extract is distilled under vacuum (130 mm) at a temperature of 25°-30° C., then the product is distilled at 70°-75° C./17 mm. to collect 12.6 g. of the desired product as a colorless liquid $n_D^{22}$ 1.4382.

EXAMPLE 9

2-Methylenehexanal

A mixture of 34.0 g. of dimethylamine hydrochloride, 31.8 g. of 37% formaldehyde and 35.0 g. of n-hexanal is stirred at 70° C. for 24 hours. The reaction mixture is then steam distilled for 3 hours. The organic distillate is dried over anhydrous magnesium sulfate and filtered to give 31.7 g. of the desired product as a colorless liquid.

EXAMPLE 10

N,O-Bis(trifluoroacetyl)hydroxylamine

To 135.2 g. of trifluoroacetic anhydride is added 14.0 g. of hydroxylamine hydrochloride. The mixture is refluxed for 2 hours then is cooled. The excess reaction solvents are removed and the residue is treated twice with hexane. The organic solvent is removed in vacuo. The product is recrystallized twice from dichloromethane to give 35.4 g. of the desired product as white crystals, 59°-60° C. (sublim.). The product is kept dry in a vacuum desicator.

EXAMPLE 11

2-Methylenehexanenitrile

To 500 ml. of dry benzene is added 8.96 g. of 2-methylenehexanal (Example 9), 32.0 ml. of pyridine and 35.0 g. of N,O-bis(trifluoroacetyl)hydroxylamine (Example 10). The reaction mixture is refluxed for 3 hours then is cooled. The solution is washed with three 50 ml. portions of saturated sodium chloride, dried over anhydrous magnesium sulfate and filtered. The filtrate is concentrated in vacuo in a water bath maintained at 40°-50° C. to give a yellow gum. The gum is distilled in a vigreaux column and the fraction b.p. 72°-76° C./50 mm. is collected to give 3.8 g. of the desired product as a colorless liquid.

EXAMPLES 12-43

Additional 3-amino-1-halogenated phenyl-2-pyrazoline compounds listed in Table I have been prepared by following the general procedure: where 0.1 moles of sodium metal is dissolved in absolute ethanol (50-200 ml.). To this solution is added the appropriate hydrazine salt or free base (0.1 moles) and after a few minutes (5-30 minutes) the appropriate nitrile (0.1 moles). The reaction mixture is refluxed (4-20 hours) after which period the solvent is removed in vacuo. The addition of water gives a filterable solid which is dissolved in dichloromethane. This solution is passed through an adsorbent column to remove impurities, then the effluent is refluxed with the gradual addition of hexane until crystallization is noted. Recrystallization from the same solvent pair (with or without another adsorbent treatment) or from acetone-hexane and/or ether-hexane provides the desired products.

TABLE I

| Example | Compound | Hydrazine | Nitrile | M.P. °C. | Crystallization Solvent |
|---|---|---|---|---|---|
| 12 | 3-Amino-1-(3,4-dichlorophenyl)-4-methyl-2-pyrazoline | 3,4-Dichlorophenylhydrazine hydrochloride | Methacrylonitrile | 131-132.5 | Dichloromethane/-Hexane |
| 13 | 3-Amine-1-(3,4-dichlorophenyl)-5-phenyl-2-pyrazoline | 3,4-Dichlorophenylhydrazine hydrochloride | Cinnamonitrile | 166-168.5 | Dichloromethane/-Hexane |
| 14 | 3-Amine-1-(3,5-dichlorophenyl)-2-pyrazoline | 3,5-Dichlorophenylhydrazine hydrochloride | Acrylonitrile | 158-159 | Acetone/Hexane |
| 15 | 3-Amino-1,5-bis(p-chlorphenyl)-2-pyrazoline | p-Chlorophenylhydrazine hydrochloride | p-Chlorocinnamonitrile | 149-150 | Acetone/Hexane |
| 16 | 3-Amino-1-(2,5-dichlorophenyl)-2-pyrazoline | 2,5-Dichlorophenylhydrazine hydrochloride | Acrylonitrile | 136-138 | Acetone/Hexane |
| 17 | 3-Amino-1-(p-chlorophenyl)-2-pyrazoline | p-Chlorophenylhydrazine hydrochloride | Acrylonitrile | 142.5-145 | Dichloromethane/-Hexane |
| 18 | 3-Amino-1-(2,4-dichlorophenyl)-2-pyrazoline | 2,4-Dichlorophenylhydrazine hydrochloride | Acrylonitrile | 169-172 | Dichloromethane/-Hexane |
| 19 | 3-Amino-1-(m-chlorophenyl)-2-pyrazoline | m-Chlorophenylhydrazine | Acrylonitrile | 131-132 | Acetone/Hexane |
| 20 | 3-Amino-1-(3,4-dichlorophenyl)-5-methyl-2-pyrazoline | 3,4-Dichlorophenylhydrazine hydrochloride | Crotononotrile | 102-104 | Acetone/Hexane |
| 21 | 3-Amino-1-(p-fluorophenyl)-2-pyrazoline | p-Fluorophenylhydrazine hydrochloride | Acrylonitrile | 115-116 | Dichloromethane/Hexane |
| 22 | 3-Amino-1-(p-fluorophenyl)-4-methyl-2 pyrazoline | p-Fluorophenylhydrazine hydrochloride | Methacrylonitrile | 123-124 | Dichloromethane/-Hexane |
| 23 | 3-Amino-5-(p-chlorophenyl)-1-(3,4-dichlorophenyl)-2-pyrazoline | 3,4-Dichlorophenylhydrazine hydrochloride | p-Chlorocinnamonitrile | 124-126.5 | Dichloromethane/Hexane |
| 24 | 3-Amino-5-(p-chlorophenyl)-1-(m-fluorophenyl)-1-pyrazoline | m-Fluorophenylhydrazine hydrochloride | p-Chlorocinnamonitrile | 135.5-136 | Dichloromethane/-Hexane |
| 25 | 3-Amino-1-(3,4-dichlorophenyl)-5-p-tolyl-2-pyrazoline | 3,4-Dichlorophenylhydrazine hydrochloride | p-Methylcinnamonitrile | 119-120 | Acetone/Hexane |
| 26 | 3-Amino-1-(p-fluorophenyl)-5-methyl-2- | p-Fluorophenylhydrazine hydrochloride | Crotononitrile | 133-135 | Dichloromethane/-Hexane |

TABLE I-continued

| Example | Compound | Hydrazine | Nitrile | M.P. °C. | Crystallization Solvent |
|---|---|---|---|---|---|
| | pyrazoline | | | | |
| 27 | 3-Amino-1-(m-fluorophenyl)-5-methyl-2-pyrazoline | m-Fluorophenylhydrazine hydrochloride | Crotononitrile | 65–67 | Dichloromethane/-Hexane |
| 28 | 3-Amino-1-(p-chlorophenyl)-5-methyl-2-pyrazoline | p-Chlorophenylhydrazine hydrochloride | Crotononitrile | 90–92 | Acetone/Hexane |
| 29 | 3-Amino-1,5-bis(3,4-dichlorophenyl)-2-pyrazoline | 3,4-Dichlorophenylhydrazine hydrochloride | 3',4'-Dichlorocinnamonitrile | 124–126 | Dichloromethane/-Hexane |
| 30 | 3-Amino-5-(p-chlorophenyl)-1-(p-fluorophenyl)-2-pyrazoline | p-Fluorophenylhydrazine hydrochloride | p-Chlorocinnamonitrile | 182–183 | Acetone/Hexane |
| 31 | 3-Amino-1-(p-chlorophenyl)-5-ethyl-2-pyrazoline | p-Chlorophenylhydrazine hydrochloride | α-Methylcrotononitrile | 117–118 | Dichloromethane/-Hexane |
| 32 | 3-Amino-1-(3,4-dichlorophenyl)-5-ethyl-2-pyrazoline | 3,4-Dichlorophenylhydrazine hydrochloride | α-Methylcrotono- | 80–83 | Dichloromethane/-Hexane |
| 33 | 3-Amino-5-ethyl-1-(p-fluorophenyl)-2-pyrazoline | p-Fluorophenylhydrazine hydrochloride | α-Methylcrotono- | 139–141 | Dichloromethane/-Hexane |
| 34 | 3-Amino-1-(p-chlorophenyl)-4-methyl-2-pyrazoline | p-Chlorophenylhydrazine hydrochloride | Methylacrylonitrile | 107–108 | Ether/Hexane |
| 35 | 3-Amino-1-(m-chlorophenyl)-4-methyl-2-pyrazoline | m-Chlorophenylhydrazine hydrochloride | Methylacrylonitrile | 85–86 | Ether/Hexane |
| 36 | 3-Amino-5-butyl-1-(p-fluorophenyl)-2-pyrazoline | p-Fluorophenylhydrazine hydrochloride | 2-Hepteneitrile | 70–72 | Dichloromethane/-Hexane |
| 37 | 3-Amino-5-butyl-1-(p-chlorophenyl)-2-pyrazoline | p-Chlorophenylhydrazine hydrochloride | 2-Heptenenitrile | 94–95 | Ether/Hexane |
| 38 | 3-Amino-4-butyl-1-(p-chlorophenyl)-2-pyrazoline | p-Chlorophenylhydrazine hydrochloride | 2-Methylenehexanenitrile | 111.5–112 | Dichloromethane/-Hexane |
| 39 | 3-Amino-1-(p-chlorophenyl)-5-propyl-2-pyrazoline | p-Chlorophenylhydrazine hydrochloride | 2-Heptenenitrile | 90–92 | Ether/Hexane |
| 40 | 3-Amino-1-(3-chloro-p-tolyl)-5-methyl-2-pyrazoline | 3-Chloro-4-methylphenylhydrazine hydrochloride | Crotononitrile | 125–126 | Ether/Hexane |
| 41 | 3-Amino-1-(m-fluorophenyl)-5-ethyl-2-pyrazoline | m-Fluorophenylhydrazine hydrochloride | 3-Methoxyvaleronitrile | 86–88 | Ether/Hexane |
| 42 | 3-Amino-1-(p-fluorophenyl)-5-phenyl-2-pyrazoline | p-Fluorophenylhydrazine hydrochloride | Cinnamonitrile | 160–161 | Dichloromethane/-Hexane |
| 43 | 3-Amino-1-(p-chlorophenyl)-5-phenyl-2-pyrazoline | p-Chlorlophenylhydrazine hydrochloride | Cinnamonitrile | 159–161 | Dichloromethane/-Hexane |

EXAMPLE 44

3-Amino-1-(p-fluorophenyl)-5-methyl-2-pyrazoline sulfate (2:1)

A mixture of 4.0 g. of 3-amino-1-(p-fluorophenyl)-5-methyl-2-pyrazoline (prepared as described in Example 26), 25.0 ml. of water and 1.0 ml. of concentrated sulfuric acid is refluxed for 6 hours. The mixture is cooled and the precipitate is collected and the solid is recrystallized first from acetone-hexane, then from acetone to give 1.0 g. of the desired product as prisms, m.p. 164.5°–166.5° C.

EXAMPLE 45

3-Amino-1-(3,4-dichlorophenyl)-5-methyl-2-pyrazoline sulfate (2:1)

A mixture of 1.0 g. of 3-amino-1-(3,4-dichlorophenyl)-5-methyl-2-pyrazoline (prepared as described in Example 20), 10 ml. of water and 0.5 ml. of concentrated sulfuric acid gives an immediate precipitate. The precipitate is collected and washed with dichloromethane. The material is then recrystallized from acetone-hexane to give 0.60 g. of the desired product as prisms, m.p. 160.5°–163° C.

EXAMPLE 46

3-Amino-1-(2,4-dichlorophenyl)-5-methyl-2-pyrazoline

A mixture of 7.8 g. of 2,4-dichlorophenylhydrazine (prepared from 2,4-dichlorohydrazine hydrochloride by treatment with 1 N sodium hydroxide), 9.9 g. of crotononitrile and 3 drops of choline (45% in methanol) is heated on a steam bath for 18 hours. The solution is mixed with 200 ml. of water then 20 ml. of concentrated hydrochloric acid is added and the mixture is refluxed for ½ hour, cooled and made basic with 10% sodium hydroxide to give a gummy solid. The solid is placed on a chromatography column containing 300 g. of a 200 mesh synthetic magnesium silicate adsorbent. The column is eluted with 1% acetone-hexane, 5% acetone-hexane and 10% acetone-hexane to remove most of the less polar material. The elution procedure is monitored by thin layer chromatography using the upper phase of a mixture of 2 parts benzene, one part acetone and 2 parts water; then the column is eluted with acetone to remove the crude product as a dark oil which partly crystallizes on standing. This material is chromatographed again using another 200 g. of the magnesium silicate adsorbent and eluting a colored impurity with 5% acetone-hexane. The column is then eluted with 50% acetone-hexane to collect a tan oil which solidifies on standing. The solid is recrystallized 3 times from ether-hexane to give 0.5 g. of the product of the Example as tan crystals, m.p. 109°-111° C.

EXAMPLE 47

Preparation of Compressed Tablet

| Ingredient | mg./tablet |
|---|---|
| Active Compound | 0.5-500 |
| Dibasic Calcium Phosphate N.F. | qs |
| Starch USP | 40 |
| Modified Starch | 10 |
| Magnesium Stearate USP | 0.1-5.0 (% w/w) |

EXAMPLE 48

Preparation of Compressed Tablet

| Ingredient | mg./tablet |
|---|---|
| Active Compound | 0.5-500 |
| Dibasic Calcium Phosphate N.F. | qs |
| Starch USP | 40 |
| Modified Starch | 10 |
| *Surfactant, e.g. Sodium Lauryl Sulfate | 0.1-2.0 (% w/w) |
| Magnesium Stearate USP | 0.1-5.0 (% w/w) |

*Other surface active agents such as disodium sulfosuccinate and nonionic surface active agents such as Span ® and Tween ® may also be employed.

EXAMPLE 49

Preparation of Compressed Tablet

| Ingredient | mg./tablet |
|---|---|
| Active Compound | 0.5-500 |
| Direct Compression Sugar Agent e.g. Emdex | qs |
| Magnesium Stearate | 0.1-3.0 (% w/w) |

EXAMPLE 50

Preparation of Hard Shell Capsule

| Ingredient | mg./capsule |
|---|---|
| Active Compound | 0.5-500 |
| Lactose, Spray Dried | qs |
| Magnesium Stearate | 0.1-3.0 (% w/w) |

EXAMPLE 51

Preparation of Oral Liquid (Syrup)

-continued

| Ingredient | % w/v |
|---|---|
| Active Compound | 0.05-5 |
| Liquid Sugar | 75.0 |
| Methyl Paraben USP | 0.18 |
| Propyl Paraben USP | 0.02 |
| Suspending Agent | 0.5-1.0 |
| e.g. Avicel | |
| Flavoring Agent | qs |
| Purified Water qs ad | 100.0 |

EXAMPLE 52

Preparation of Oral Liquid (Elixir)

| Ingredient | % w/v |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 53

Preparation of Oral Suspension (Syrup)

| Ingredient | % w/v |
|---|---|
| Active Compound | 0.05-5 |
| Polysorbate 80 USP | 0.1 |
| Magnesium Aluminum Silicate, Colloidal | 0.3 |
| Dye | 0.001-0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 54

Preparation of Injectable Solution

| Ingredient | % w/v |
|---|---|
| Active Compound | 0.05-5 |
| Benzyl Alcohol N.F. | 0.9 |
| Water for Injection | 100.0 |

EXAMPLE 55

Preparation of Injectable Oil

| Ingredient | % w/v |
|---|---|
| Active Compound | 0.05-5 |
| Benzyl Alcohol | 1.5 |
| Sesame Oil qs ad | 100.0 |

EXAMPLE 56

Preparation of Intra-articular Product

| Ingredient | Amount |
|---|---|
| Active Compound | 2-20 mg. |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 57

Preparation of Injectable Depo Suspension

| Ingredient | % w/v |
|---|---|
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 58

Preparation of Topical Cream

| Ingredient | % w/w |
|---|---|
| Active Compound | 0.05-5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 59

Preparation of Topical Ointment

| Ingredient | % w/w |
|---|---|
| Active Compound | 0.05-5 |
| Cholesterol | 3 |
| Stearyl Alcohol | 3 |
| White Wax | 8 |
| Petrolatum, White USP qs | 100 |

We claim:

1. A method of meliorating inflammation in a mammal which comprises administering to said mammal an effective anti-inflammatory amount of a compound selected from those of the formula:

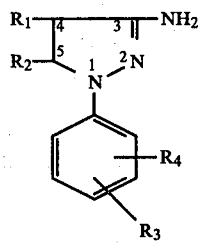

wherein $R_1$ is hydrogen or lower alkyl ($C_1$–$C_4$); $R_2$ is phenyl or

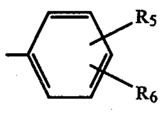

where $R_5$ and $R_6$ are the same or different and are hydrogen, halogen or lower alkyl ($C_1$–$C_4$) with the proviso that $R_5$ and $R_6$ cannot both be hydrogen; $R_3$ and $R_4$ are the same or different and are hydrogen or halogen with the proviso that $R_3$ and $R_4$ cannot both be hydrogen; and the pharmacologically acceptable acid-addition salts thereof.

2. A method according to claim 1, wherein the compound is 3-amino-1,5-bis(p-chlorophenyl)-2-pyrazoline.

3. A method according to claim 1, wherein the compound is 3-amino-1-(p-fluorophenyl)-5-phenyl-2-pyrazoline.

4. A method according to claim 1, wherein the compound is 3-amino-1-(p-chlorophenyl)-5-phenyl-2-pyrazoline.

5. A method of treating pain in a mammal which comprises administering to said mammal an effective analgesic amount of a compound of the formula:

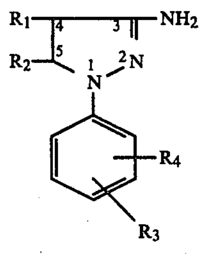

wherein $R_1$ is hydrogen or lower alkyl ($C_1$–$C_4$); $R_2$ is phenyl or

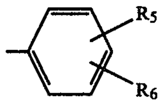

where $R_5$ and $R_6$ are the same or different and are hydrogen, halogen or lower alkyl ($C_1$–$C_4$) with the proviso that $R_5$ and $R_6$ cannot both be hydrogen; $R_3$ and $R_4$ are the same or different and are hydrogen or halogen with the proviso that $R_3$ and $R_4$ cannot both be hydrogen; and the pharmacologically acceptable acid-addition salts thereof.

6. A method according to claim 5 wherein the compound is 3-amino-1-(3,4-dichlorophenyl)-5-phenyl-2-pyrazoline.

7. A method according to claim 5 wherein the compound is 3-amino-1,5-bis(p-chlorophenyl)-2-pyrazoline.

8. A method according to claim 5 wherein the compound is 3-amino-5-(p-chlorophenyl)-1-(m-fluorophenyl)-1-pyrazoline.

9. A method according to claim 5 wherein the compound is 3-amino-1-(3,4-dichlorophenyl)-5-p-tolyl-2-pyrazoline.

10. A method according to claim 5 wherein the compound is 3-amino-1,5-bis(3,4-dichlorophenyl)-2-pyrazoline.

11. A method according to claim 5 wherein the compound is 3-amino-1-(p-fluorophenyl)-5-phenyl-2-pyrazoline.

12. A method according to claim 5 wherein the compound is 3-amino-1-(p-chlorophenyl)-5-phenyl-2-pyrazoline.

13. A method of treating bacterial and/or fungal infections in a mammal which comprises administering to said mammal an effective antibacterial and/or antifungal amount of a compound selected from those of the formula:

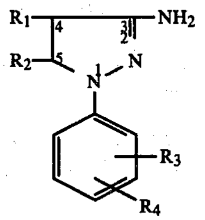

wherein $R_1$ is hydrogen or lower alkyl ($C_1$–$C_4$); $R_2$ is hydrogen, lower alkyl ($C_1$–$C_4$), phenyl or

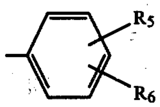

where $R_5$ and $R_6$ are the same or different and are hydrogen, halogen or lower alkyl ($C_1$–$C_4$) with the proviso that $R_5$ and $R_6$ cannot both be hydrogen; $R_3$ and $R_4$ are the same or different and are hydrogen or halogen with the proviso that $R_3$ and $R_4$ cannot both be hydrogen; and the pharmacologically acceptable acid-addition salts thereof.

14. A method according to claim 13 wherein the compound is 3-amino-1-(m-chlorophenyl)-5-phenyl-2-pyrazoline.

15. A method according to claim 13 wherein the compound is 3-amino-1-(m-fluorophenyl)-5-phenyl-2-pyrazoline.

16. A method according to claim 13 wherein the compound is 3-amino-1-(3,4-dichlorophenyl)-5-phenyl-2-pyrazoline.

17. A method according to claim 13 wherein the compound is 3-amino-1,5-bis(p-chlorophenyl)-2-pyrazoline.

18. A method according to claim 13 wherein the compound is 3-amino-5-(p-chlorophenyl)-1-(3,4-dichlorophenyl)-2-pyrazoline.

19. A method according to claim 13 wherein the compound is 3-amino-5-(p-chlorophenyl)-1-(m-fluorophenyl)-1-pyrazoline.

20. A method according to claim 13 wherein the compound is 3-amino-1-(3,4-dichlorophenyl)-5-p-tolyl-2-pyrazoline.

21. A method according to claim 13 wherein the compound is 3-amino-1,5-bis(3,4-dichlorophenyl)-2-pyrazoline.

22. A method according to claim 13 wherein the compound is 3-amino-5-(p-chlorophenyl)-1-(p-fluorophenyl)-2-pyrazoline.

23. A method according to claim 13 wherein the compound is 3-amino-1-(p-fluorophenyl)-5-phenyl-2-pyrazoline.

24. A method according to claim 13 wherein the compound is 3-amino-1-(p-chlorophenyl)-5-phenyl-2-pyrazoline.

25. A method according to claim 13 wherein the compound is 3-amino-1-(3,4-dichlorophenyl)-2-pyrazoline.

26. A method according to claim 13 wherein the compound is 3-amino-1-(m-fluorophenyl)-4-methyl-2-pyrazoline.

27. A method according to claim 13 wherein the compound is 3-amino-1-(m-fluorophenyl)-2-pyrazoline.

28. A method according to claim 13 wherein the compound is 3-amino-1-(3,4-dichlorophenyl)-2-pyrazoline hydrochloride.

29. A method according to claim 13 wherein the compound is 3-amino-1-(3,4-dichlorophenyl)-4-methyl-2-pyrazoline.

30. A method according to claim 13 wherein the compound is 3-amino-1-(3,5-dichlorophenyl)-2-pyrazoline.

31. A method according to claim 13 wherein the compound is 3-amino-1-(2,5-dichlorophenyl)-2-pyrazoline.

32. A method according to claim 13 wherein the compound is 3-amino-1-(p-chlorophenyl)-2-pyrazoline.

33. A method according to claim 13 wherein the compound is 3-amino-1-(2,4-dichlorophenyl)-2-pyrazoline.

34. A method according to claim 13 wherein the compound is 3-amino-1-(m-chlorophenyl)-2-pyrazoline.

35. A method according to claim 13 wherein the compound is 3-amino-1-(3,4-dichlorophenyl)-5-methyl-2-pyrazoline.

36. A method according to claim 13 wherein the compound is 3-amino-1-(p-fluorophenyl)-2-pyrazoline.

37. A method according to claim 13 wherein the compound is 3-amino-1-(p-fluorophenyl)-4-methyl-2-pyrazoline.

38. A method according to claim 13 wherein the compound is 3-amino-1-(p-fluorophenyl)-5-methyl-2-pyrazoline.

39. A method according to claim 13 wherein the compound is 3-amino-1-(m-fluorophenyl)-5-methyl-2-pyrazoline.

40. A method according to claim 13 wherein the compound is 3-amino-1-(p-chlorophenyl)-5-methyl-2-pyrazoline.

41. A method according to claim 13 wherein the compound is 3-amino-1-(p-chlorophenyl)-5-ethyl-2-pyrazoline.

42. A method according to claim 13 wherein the compound is 3-amino-1-(3,4-dichlorophenyl)-5-ethyl-2-pyrazoline.

43. A method according to claim 13 wherein the compound is 3-amino-5-ethyl-1-(p-fluorophenyl)-2-pyrazoline.

44. A method according to claim 13 wherein the compound is 3-amino-1-(p-chlorophenyl)-4-methyl-2-pyrazoline.

45. A method according to claim 13 wherein the compound is 3-amino-1-(m-chlorophenyl)-4-methyl-2-pyrazoline.

46. A method according to claim 13 wherein the compound is 3-amino-5-butyl-1-(p-fluorophenyl)-2-pyrazoline.

47. A method according to claim 13 wherein the compound is 3-amino-5-butyl-1-(p-chlorophenyl)-2-pyrazoline.

48. A method according to claim 13 wherein the compound is 3-amino-4-butyl-1-(p-chlorophenyl)-2-pyrazoline.

49. A method according to claim 13 wherein the compound is 3-amino-1-(p-chlorophenyl)-5-propyl-2-pyrazoline.

50. A method according to claim 13 wherein the compound is 3-amino-1-(3-chloro-p-tolyl)-5-methyl-2-pyrazoline.

51. A method according to claim 13 wherein the compound is 3-amino-1-(m-fluorophenyl)-5-ethyl-2-pyrazoline.

52. A method according to claim 13 wherein the compound is 3-amino-1-(p-fluorophenyl)-5-methyl-2-pyrazoline sulfate (2:1).

53. A method according to claim 13 wherein the compound is 3-amino-1-(3,4-dichlorophenyl)-5-methyl-2-pyrazoline sulfate (2:1).

54. A method of meliorating inflammation or the progressive joint deterioration characteristic of arthritic disease in a mammal which comprises administering to said mammal an effective anti-inflammatory amount of a compound selected from those of the formula:

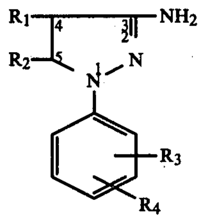

wherein $R_1$ is hydrogen or lower alkyl ($C_1$–$C_4$); $R_2$ is phenyl or

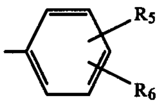

where $R_5$ and $R_6$ are the same or different and are hydrogen, halogen or lower alkyl ($C_1$–$C_4$) with the proviso that $R_5$ and $R_6$ cannot both be hydrogen; $R_3$ and $R_4$ are the same or different and are hydrogen or halogen with the proviso that $R_3$ and $R_4$ cannot both be hydrogen; and the pharmacologically acceptable acid-addition salts thereof.

55. A method according to claim 54, wherein the compound is 3-amino-1,5-bis(p-chlorophenyl)-2-pyrazoline.

56. A method according to claim 54, wherein the compound is 3-amino-1-(p-fluorophenyl)-5-phenyl-2-pyrazoline.

57. A method according to claim 54, wherein the compound is 3-amino-1-(p-chlorophenyl)-5-phenyl-2-pyrazoline.

58. A method of preventing the onset of asthmatic symptoms or allergic diseases in a mammal which comprises administering to said mammal an effective prophylactic amount for the prevention of asthmatic symptoms or allergic diseases of a compound selected from those of the formula:

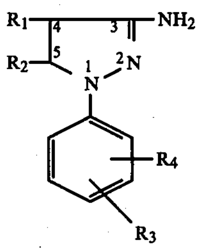

wherein $R_1$ is hydrogen or lower alkyl ($C_1$–$C_4$); $R_2$ is phenyl or

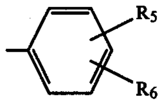

where $R_5$ and $R_6$ are the same or different and are hydrogen, halogen or lower alkyl ($C_1$–$C_4$) with the proviso that $R_5$ and $R_6$ cannot both be hydrogen; $R_3$ and $R_4$ are the same or different and are hydrogen or halogen with the proviso that $R_3$ and $R_4$ cannot both be hydrogen; and the pharmacologically acceptable acid-addition salts thereof.

* * * * *